United States Patent [19]

Hung et al.

[11] 4,331,589

[45] May 25, 1982

[54] DEOXYRIBONUCLEIC ACID SYNTHESIS USING BINDING PROTEIN EXTRACTED FROM CHICK EMBRYO FIBROBLASTS

[75] Inventors: Paul P. Hung, Waukegan; Shaw-Guang Lee, Libertyville, both of Ill.

[73] Assignee: Abbott Laboratories, North Chicago, Ill.

[21] Appl. No.: 254,726

[22] Filed: Apr. 16, 1981

Related U.S. Application Data

[60] Continuation-in-part of Ser. No. 112,267, Jan. 5, 1980, abandoned, which is a division of Ser. No. 963,245, Nov. 22, 1978, Pat. No. 4,224,408.

[51] Int. Cl.$^3$ .............................................. C07G 7/00
[52] U.S. Cl. ................................. 260/112 R; 435/91
[58] Field of Search ....................... 260/112 R; 435/91

[56] References Cited

PUBLICATIONS

The Proteins, Neurath, vol. III, 1965, pp. 20, 23 and 80–82.
Proc. Natn. Acad. Sci. USA 70, 230–234, 1973, Grandgenett et al.
A Lab Manual of Analytical Methods of Protein Chemistry, vol. I, Alexander et al., pp. 67, 73–74 and 76–78, 1960.
Nature, vol. 259, No. 5543, pp. 499–502, Feb. 12, 1976, Hung et al.
Nature, vol. 270, No. 5635, pp. 366–369, Nov. 24, 1977, Lee et al.

*Primary Examiner*—Howard E. Schain
*Attorney, Agent, or Firm*—Gildo E. Fato; Robert L. Niblack

[57] ABSTRACT

Described is a method of obtaining complete copying of the entire length of single stranded ribonucleic acid (RNA) into its complementary deoxyribonucleic acid (cDNA) by reverse transcription using binding protein. The method can be used in recombinant DNA research to copy total messenger RNA into DNA.

1 Claim, 1 Drawing Figure

DEOXYRIBONUCLEIC ACID SYNTHESIS USING BINDING PROTEIN EXTRACTED FROM CHICK EMBRYO FIBROBLASTS

BACKGROUND OF THE INVENTION

This application is a continuation-in-part application of application Ser. No. 112,267, now abandoned, filed Jan. 5, 1980 which is a divisional application of application Ser. No. 963,245, filed Nov. 22, 1978, now U.S. Pat. No. 4,224,408.

In the synthesis of deoxyribonucleic acid (DNA) it is often extremely difficult to copy the entire length of single stranded ribonucleic acid (RNA) into its complementary DNA because of the highly folded nature of the RNA. In the synthesis of complementary DNA (cDNA) from messenger RNA (mRNA) for example, it is important to copy the total length of messenger RNA into DNA, otherwise the resultant gene equivalent in the form of cDNA will be incomplete. In Nature, Volume 259, No. 5543, pages 499–502, Feb. 12, 1976 there is described the isolation of nucleic acid binding protein which is effective in unwinding the highly folded RNA so that its reverse transcription can be facilitated to yield higher quantities of DNA. This article reports the isolation of the nucleic acid binding protein from chick fibroblasts transformed by Rous sarcoma virus (RSV) and its stimulatory effect on DNA synthesis catalyzed by reverse transcriptase. As described, the binding protein is obtained using a method in which Rous sarcoma virus-transformed chicken fibroblasts are sonicated, the cells are then centrifuged to remove the debris, polyethylene glycol is added in order to remove the DNA and to obtain the supernatant, the supernatant is passed through a chromagraphic column to absorb the binding protein, and lastly, the binding protein is eluted from the column with 0.2 molar salt solution.

DRAWING

FIG. 1 is a photograph of an autoradiograph illustrating the effect of the binding protein.

DETAILED DESCRIPTION OF THE INVENTION

Figure 1:
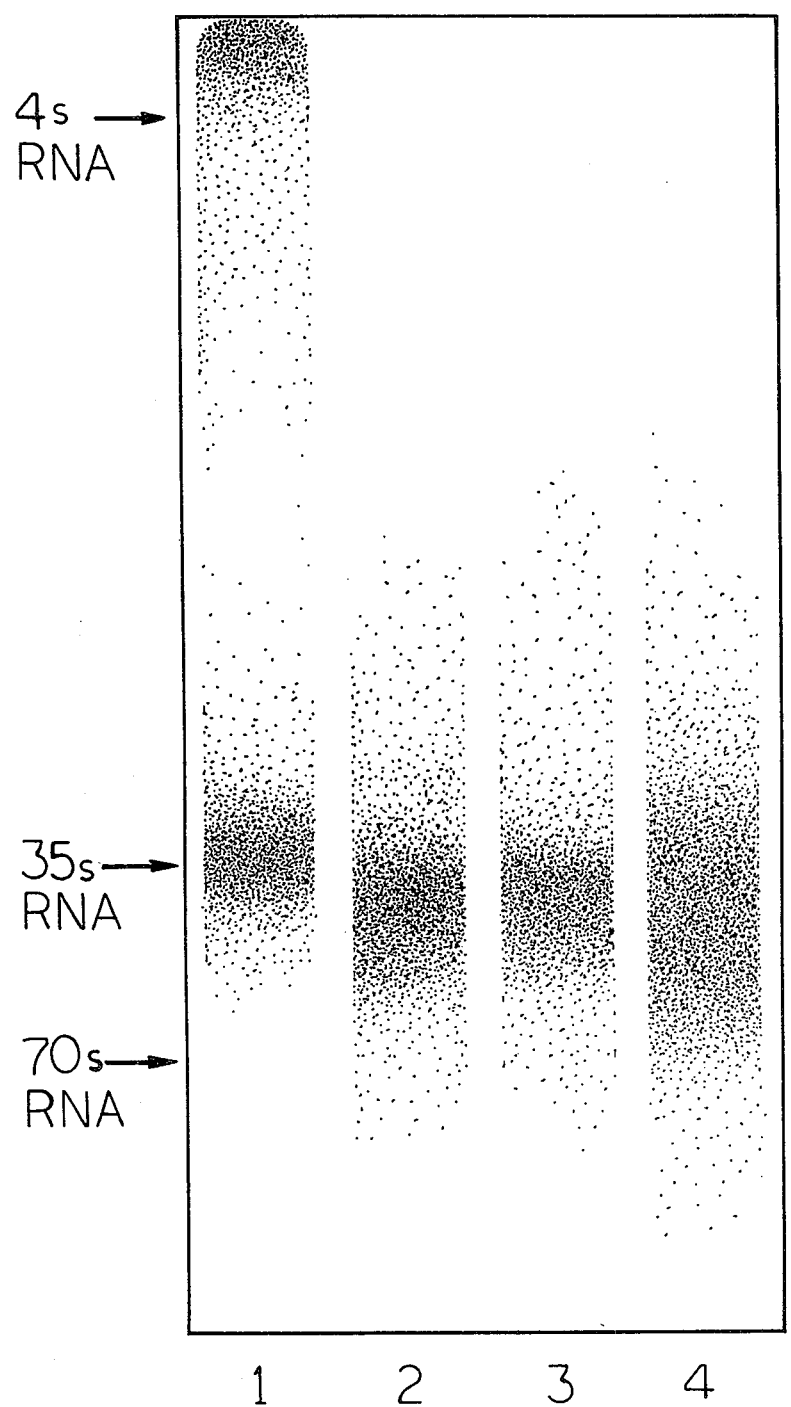

Reverse transcription of single stranded Rous sarcoma virus RNA having a sedimentation coefficient of 35 into DNA in the absence of binding protein results in a small DNA product having a similar size to transfer RNA (a sedimentation coefficient of 4), as analyzed by gel electrophoresis, indicating completed copying of only a partial length of the single stranded RNA. Reverse transcription conducted in the presence of binding protein results in a DNA product having a size of the RNA template (35 S), as analyzed by gel electrophoresis, indicating complete copying of the entire length of the single stranded RNA. Reverse transcription of Rous sarcoma virus genome using nucleic acid binding protein is described in Nature, Vol. 270, No. 5635, pages 366–369, Nov. 24, 1977. Essentially, the method comprises reverse transcription of Rous sarcoma virus RNA in the presence of binding protein, isolation of the DNA by gel filtration chromatography and electrophoresis to determine the size of the product. In recombinant DNA research, it is important to copy total messenger RNA into DNA, otherwise the gene will be fragmental. The procedure can be more fully described as follows.

EXAMPLE 1

Isolation of Nucleic Acid Binding Protein

Binding protein was isolated by affinity chromatography from chick embryo fibroblasts chronically transformed by Schmidt-Ruppin Rous sarcoma virus, subgroup D after 2 weeks of virus infection. Cellulose containing covalently linked single stranded calf thymus DNA was used. In a typical run, about 2 grams of transformed cells were washed, sonicated and centrifuged to obtain debris-free supernatant. The supernatant was treated with polyethylene glycol and centrifuged to remove nucleic acid. After dialysis the supernatant was passed through a DNA-cellulose column (1×1) pre-equilibrated with Tris buffer (20 mM Tris-HCl, pH 8.0, 1 mM ethylene diamine tetra acetate (EDTA), 1 mM 2-mercaptoethanol, 50 mM NaCl and 10% glycerol). The column was washed with the Tris buffer and then eluted stepwise with 0.2 M NaCl in the buffer. Resulting fractions were assayed for nucleic acid binding activity with a membrane filtration technique as described by Jones et al. (J. Molec. Biol., 22, 199–209, 1966) using either $^3$H-poly d(AT).poly d(AT) or $^3$H-poly(rA).poly(dT) as substrate. All the fractions containing binding protein were combined and dialyzed against the binding protein buffer (20 mM Tris-HCl, pH 8.0, 1 mM EDTA, 1 mM 2-mercaptoethanol, 20 mM NaCl and 30% glycerol). The binding activity eluted with 0.2 M NaCl was further purified by ion exhange chromatography, namely, passed through diethyl aminoethyl (DEAE) celluloses and then to a carboxymethyl (CM-BioGel) column. A single peak of binding activity as measured by the membrane filtration technique was eluted from the CM BioGel column at 0.3 M NaCl in a buffer containing 50 mM Tris-HCl, pH 8.1, 10% glycerol, 1 mM 2-mercaptoethanol, and 1 mM EDTA. This material showed a major Coomassie blue band of over 85% homogeneity after SDS (sodium dodecyl sulfate) gel electrophoresis and at least a 500-fold enrichment in the nucleic acid binding activity as compared to the crude sonicated extract. It had no detectable reverse transcriptase, DNA polymerase or nuclease activities.

The stimulatory effect of the isolated binding protein on polymerase activity was studied in a reaction in which reverse transcriptase catalyzed DNA synthesis using heat-denatured calf thymus DNA as a template. DNA synthesis as represented by TCA-insoluble counts was linearly proportional to the amount of binding protein present in the reaction with a maximum stimulation of about ten-fold increase with 1 microgram of the protein. Heating of the binding protein at 100° C. for 5 minutes completely abolished the stimulatory effect and the binding protein itself contained no polymerase activity.

Binding protein was also isolated from chick embryo fibroblasts (without transformation by RSV) by the same procedure and this protein also stimulated DNA synthesis.

EXAMPLE 2

Reverse Transcription of Single Stranded Rous sarcoma virus RNA

Incubation mixtures (0.1 ml) contained the following: 50 mM Tris-HCl, pH 8.3, 0.06 M KCl, 5 mM MgCl, 0.01 M dithiothreitol, 0.1 mM EDTA, 0.02% NP-40, 1.6 micrograms 70S RSV RNA composed of 2 subunits of 35S, 0.1 micrograms (dT)10-18, 100 micrograms per ml actinomycin D, 0.1 mM each of dATP, dCTP, dGTP, 10 microcurie [$\alpha$-$^{32}$P]TP, (1 Ci mmol$^{-1}$), 20 units of reverse transcriptase purified by the method of Grandgenett et al., (Proc. Natn. Acad. Sci. U.S.A. 70, 230-234, 1973). The reaction mixture was incubated at 37° C. for 10 minutes and the binding protein eluted at 0.3 M NaCl from the CM-BioGel column or buffer alone was added. Incubation was carried out further at 24° C. for 4 hours. At the end of the incubation, the reaction mixture was adjusted to contain 0.05 M EDTA, 0.2% sodium sarkosyl and 50 micrograms yeast RNA. The DNA product was isolated by Sephadex filtration and alkali hydrolysis according to Rothenberg and Baltimore (J. Virol., 21, 168-178, 1977). The samples thus obtained were divided into two parts, one for electrohoresis followed by autoradiography and the other for hybridization studies. Electrophoresis of the DNA products (approximately 1,000 c.p.m. per slot) was done in 0.8% Agarose gel (10 cm long) for 3.5 hours at 100 V (Meth. Virol., 5, 125-177, 1971). Non-radioactive 70S RSV RNA, 35S RSV RNA, obtained by heating and chilling of 70S (J. Virol., 10, 23-31 1972) and tRNA were co-electrophoresed.

Autoradiography (FIG. 1) was used to evaluate the effect of the binding protein. Material was added to the gel as follows: Lane 1, buffer control; Lane 2, 4 micrograms of binding protein from a preparation of transformed cells; Lane 3, 4 micrograms from another transformed cell preparation; Lane 4, 15 micrograms of binding protein from nontransformed cells.

Examination of the results (FIG. 1) of the experiment established that Lane 1 showed that when no binding protein was added most DNA products moved to the far end of the gel corresponding to a mobility of about 4 S. In Lanes 2, 3 and 4, with various preparations of binding protein added, almost all of the DNA product moved much slower and its mobility corresponded to that of 35S RSV RNA. The appearance of the large products in Lane 2, 3 and 4 was eliminated if the binding protein solution was first heated to 65° C. for 10 minutes.

The results presented here show that reverse transcriptase from RSV is able to synthesize, in a reconstructed system, a complete or nearly complete DNA copy from the purified viral RNA in the presence of the binding protein isolated from chicken cells.

We claim:

1. In the improved method of isolating nucleic acid binding protein from Rous sarcoma virus transformed or nontransformed chick embryonic fibroblast cells, said method comprising:
   sonicating said cells;
   separating the supernatant from the sonicated cells;
   passing the supernatant through an affinity column comprising DNA to absorb the binding protein;
   eluting the binding protein with a salt solution;
   the improvement which consists essentially of further purifying the binding protein by ion exchange chromatography comprising first passing the eluate through a diethylaminoethyl cellulose column to absorb nucleases, undesired enzymes, and other binding protein unrelated to the desired protein and obtain a leak-through, and then subsequently passing the leak-through material through a carboxymethyl cellulose column to absorb the nucleic acid binding protein and other unrelated binding proteins and then eluting the desired binding protein specifically with a salt solution.

* * * * *